United States Patent [19]

Rodini

[11] Patent Number: 4,980,031

[45] Date of Patent: Dec. 25, 1990

[54] SOLVENT RECOVERY

[75] Inventor: David J. Rodini, Midlothian, Va.

[73] Assignee: E. I. Du Pont de Nemours and Company, Wilmington, Del.

[21] Appl. No.: 475,926

[22] Filed: Feb. 6, 1990

Related U.S. Application Data

[63] Continuation-in-part of Ser. No. 388,403, Aug. 2, 1989, abandoned.

[51] Int. Cl.$^5$ .............................................. B01D 3/34
[52] U.S. Cl. .................................... 203/7; 202/267.1; 203/59; 203/86; 564/216; 570/262
[58] Field of Search .................. 203/6, 7, 59, 86, 68, 203/28, DIG. 6, 14; 202/267.1; 570/262; 564/216

[56] References Cited

U.S. PATENT DOCUMENTS

| | | |
|---|---|---|
| 2,543,575 | 2/1951 | Harvey et al. ............................ 203/6 |
| 3,790,496 | 2/1974 | Hausler ................................. 203/7 |
| 3,919,054 | 11/1975 | Hands ................................... 203/7 |
| 3,981,780 | 9/1976 | Scherrer et al. ......................... 203/7 |
| 4,062,764 | 12/1977 | White et al. ............................ 203/7 |
| 4,115,530 | 9/1978 | Coenen et al. .......................... 203/7 |
| 4,566,973 | 1/1986 | Masler, III et al. ................... 203/12 |
| 4,628,836 | 12/1986 | Littmann ................................ 203/7 |

FOREIGN PATENT DOCUMENTS

| | | | |
|---|---|---|---|
| 0610634 | 12/1960 | Canada ................................... 203/6 |
| 1115424 | 5/1968 | United Kingdom ................ 564/216 |

Primary Examiner—Virginia Manoharan

[57] ABSTRACT

Hydrogen chloride evolution is reduced in the distillation of chloroform from its admixture with an amide solvent when in contact with stainless steel, by incorporation of certain tertiary aliphatic amines.

3 Claims, No Drawings

SOLVENT RECOVERY

BACKGROUND OF THE INVENTION

This application is a continuation-in-part of application Ser. No. 07/388,403 filed on Aug. 2, 1989, now abandoned.

DESCRIPTION OF THE PRIOR ART

Aliphatic amide solvents are employed in a variety of industrial processes. In certain of these processes the effluent stream consists of the amide solvent and water which must be removed to permit recycling of the amide solvent. Conventional distillation can achieve the separation but this involves high energy consumption since the water has a high heat of vaporization and is first to distill off from the mixture.

To mitigate the effect of high energy consumption, it has been proposed to combine the amide solvent/water stream with chloroform which preferentially dissolves the amide solvent and permits separation from the water by decanting. This procedure yields an amide solvent/chloroform solution from which the chloroform must be distilled if the amide solvent is to be recycled. This involves energy saving since the chloroform is removed from the amide with expenditure of less energy than for the removal of water. Attempts to distill off the chloroform in stainless steel apparatus have presented yet another problem, namely corrosion of the apparatus. This is believed caused by hydrogen chloride evolved due to degradation of the amide-chloroform mixture. The present invention addresses the problem.

SUMMARY OF THE INVENTION

This invention provides a novel composition comprising a solution of chloroform and an aliphatic amide solvent and an amount of a tertiary aliphatic amine selected from the group consisting of triethyl amine, tripropyl amine, tributyl amine, trioctyl amine and diisopropylethyl amine in an amount sufficient to suppress formation of hydrogen chloride and reduce corrosion when the solution is distilled d in contact with stainless steel for removal of chloroform and recovery of the amide solvent.

Also provided is a process for the recovery of an aliphatic amide solvent from a solution of chloroform and the amide solvent while the solution is in contact with stainless steel which comprises, adding a tertiary aliphatic amine selected from the group consisting of triethyl amine, tripropyl amine, tributyl amine, trioctyl amine and diisopropylethyl amine, to the solution of chloroform and amide to suppress formation of hydrogen chloride, distilling the solution to drive off the chloroform and recover the amide solvent.

DETAILED DESCRIPTION OF THE INVENTION

In certain chemical operations as in the spinning of poly(meta-phenylene isophthalamide) filaments from solutions containing dimethylacetamide (DMAc), calcium chloride and water, and subsequent coagulation of the spun filaments with an aqueous bath as described in U.S. Pat. No. 3,756,908, solutions of DMAc and water are obtained from which the DMAc must be retrieved for recycling in the process. In other instances, it is desired to separate and recover N-methylpyrrolidone (NMP) from water. One way which has been proposed to effect separation of the amide solvent from the water has been to treat the mixture with chloroform to preferentially dissolve the amide solvent and then to decant the water layer. To recover the amide solvent from its solution with the chloroform, distillation of the chloroform from the solution in a stainless steel apparatus is the method of choice. It has been found that the combination of the amide solvent-chloroform mixture in contact with stainless steel during the distillation process promotes evolution of hydrogen chloride which in turn causes substantial corrosion of the stainless steel apparatus. Applicant has found that incorporation of an inhibiting amount of certain tertiary aliphatic amines, suppresses the evolution of hydrogen chloride and substantially reduces the corrosion.

The invention is applicable to aliphatic amide solvent-chloroform solutions of varying proportions. As a practical matter one desiring to separate and recover aliphatic amide solvent from its solution in water would add a sufficient amount of chloroform to preferentially take up substantially all of the amide solvent to permit separation of the water layer from the amide solvent-chloroform layer as by decanting. The addition of an excess amount of chloroform beyond that needed to take up the amide solvent would be wasteful since the chloroform must subsequently be separated by distillation from the amide solvent. On the other hand the addition of an amount of chloroform inadequate to take up the amide solvent present in the aqueous solution of amide solvent would reduce the recovery of amide solvent.

When first separated from the water layer, the chloroform may constitute from 20 to 30% by weight of the solution of amide solvent plus chloroform. During the distillation of the solution, the concentration of chloroform decreases as the distillation proceeds and chloroform is driven off. The corrosion rate appears to be greater at those sections of the distillation column where these less concentrated solutions are present.

The amide solvent-chloroform solution, as separated from the water layer may contain inorganic salts as well as small amounts of water. The presence of these ingredients is not seen to interfere with the advantages obtained in the present invention.

As mentioned previously, the selected tertiary aliphatic amine should be added to the amide solvent-chloroform mixture that is to be distilled or is being distilled and it should be added in an amount that is sufficient to reduce corrosion of the stainless steel apparatus. Suitable tertiary aliphatic amines include triethyl amine, tripropyl amine, tributyl amine, trioctyl amine and diisopropylethyl amine. A small amount, generally at least 0.5% by weight based on the weight of the chloroform in the solution to be distilled has been found satisfactory for the purpose. Amounts greater than 10% would appear to unduly increase costs without concomitant advantage.

The following examples are illustrative of the invention (except for the controls) and are not to be construed as limiting.

EXAMPLES 1–8

A Soxhlet extractor is set up using a 500 ml or a 1000 ml round bottomed flask. The apparatus is dried overnight in an oven. Stainless steel coupons (SS304) are cleaned and dried. The experimental apparatus is set-up and a dried coupon of SS304 is added to the round bottomed flask. The apparatus is blanketed with nitrogen. Addition of DMAc and chloroform and trialkyl amine to the system is under nitrogen via airless syringes. The solution in the round bottomed flask is refluxed for 16 hours. (In practice the chloroform that is distilled off would be removed and the amide solvent recovered.) The solution is then cooled to room temperature, the metal coupon is dried and weighed and the % wt. loss reported.

The table below identifies the trialkyl amine and reports the relative proportions of the solution components and the % wt. loss of the coupon.

TABLE

| Ex. | Chloroform Wt. % | Amine | Amine Wt. % | Amide Wt. % | % Wt. Loss |
|---|---|---|---|---|---|
| 1 | 100 | None | 0 | 0 | 0 |
| 2 | 1 | None | 0 | 99 | 5.96 |
| 3 | 1 | TBA* | 0.76 | 97.44 | 0.05 |
| 4 | 1.05 | TBA* | 1.56 | 97.39 | 0.0112 |
| 5 | 0.97 | TBA* | 0.47 | 98.56 | 0.02 |
| 6 | 0.87 | TOA** | 0.37 | 98.79 | 1.61 |
| 7 | 0.85 | DIEA*** | 0.29 | 98.86 | 0.66 |
| 8 | 0.85 | TPA**** | 0.76 | 98.39 | 0.41 |

*tributyl amine
**trioctyl amine
***diisopropylethyl amine
****tripropyl amine

EXAMPLE 9

A 1 liter 3-necked flask is dried in an oven until free of moisture and fItted wIth a chilled water condenser. A Teflon coated magnetic stirring bar is employed to stir the solution. The temperature of the solution in the flask is measured by a thermometer and maintained via a heating mantle which is controlled by a rheostat.

To the flask as described above is added 700 ml of a solution consisting of 8.2% chloroform, 0.5% water, 0.06% tributyl amine (0.73% by weight base d on chloroform content) and 91.24% dimethyl acetamide and coupon of 304 stainless steel. This solution is stirred and heated at 148° C. for 16 hours. At the end of this time period, the corrosion rate, as determined based on the weight loss of the metal coupon, was 0 mils/year.

In a control experiment, there is added to a similarly prepared flask, a coupon of 304 stainless steel, and 700 ml of a solution consisting of 7.9% chloroform, 0.5% water and 91.60% dimethyl acetamide. The solution is stirred and heated at 149° C. for 16 hours. At the end of this time period the corrosion rate is measured. Based on the weight loss of the metal coupon, it was calculated to be 9.7 mils/year.

I claim:

1. A process for recovery of an aliphatic amide solvent from a solution of chloroform and the amide solvent while the solution is in contact with stainless steel which consists essentially of adding a tertiary aliphatic amine selected from the group consisting of triethyl amine, tripropyl amine, tributyl amine, trioctyl amine and diisopropylethyl amine, to the solution of chloroform and amide in an amount of at least 0.5% by weight, based on the weight of chloroform in the solution, to suppress formation of hydrogen chloride and substantially reduce corrosion, distilling the solution to drive off the chloroform and recovering the amide solvent.

2. The process of claim 1 wherein the tertiary aliphatic amine is tributyl amine.

3. The process of claim 1 wherein the amide solvent is selected from the group consisting of dimethylacetamide and N-methylpyrrolidone.

* * * * *